(12) United States Patent
McCormick

(10) Patent No.: US 11,892,124 B2
(45) Date of Patent: Feb. 6, 2024

(54) CRYOGENIC STORAGE CONTAINER CLOSURE

(71) Applicant: Savsu Technologies LLC, Old Bethpage, NY (US)

(72) Inventor: Bruce McCormick, Sante Fe, NM (US)

(73) Assignee: SAVSU TECHNOLOGIES LLC, Bothell, WA (US)

( * ) Notice: Subject to any disclaimer, the term of this patent is extended or adjusted under 35 U.S.C. 154(b) by 428 days.

(21) Appl. No.: 16/119,672

(22) Filed: Aug. 31, 2018

(65) Prior Publication Data

US 2019/0063688 A1 Feb. 28, 2019

Related U.S. Application Data

(60) Provisional application No. 62/552,849, filed on Aug. 31, 2017.

(51) Int. Cl.
| | |
|---|---|
| *F17C 13/06* | (2006.01) |
| *F17C 13/00* | (2006.01) |
| *F17C 13/02* | (2006.01) |
| *A01N 1/02* | (2006.01) |
| *A61M 1/00* | (2006.01) |

(52) U.S. Cl.
CPC ............ *F17C 13/06* (2013.01); *A01N 1/0257* (2013.01); *A61M 1/00* (2013.01); *F17C 13/001* (2013.01); *F17C 13/026* (2013.01); *F17C 2205/0311* (2013.01); *F17C 2205/0338* (2013.01); *F17C 2223/0161* (2013.01); *F17C 2250/0439* (2013.01); *F17C 2250/0478* (2013.01); *F17C 2250/0491* (2013.01)

(58) Field of Classification Search
CPC ...... F17C 13/06; F17C 13/001; F17C 13/026; F17C 2205/0311; F17C 2205/0338; F17C 2223/0161
See application file for complete search history.

(56) References Cited

U.S. PATENT DOCUMENTS

| | | | | |
|---|---|---|---|---|
| 2,648,953 | A | * 8/1953 | Sulfrian | F17C 13/06 |
| | | | | 62/47.1 |
| 3,460,740 | A | * 8/1969 | Hagen | B65D 81/052 |
| | | | | 206/523 |
| 3,489,311 | A | * 1/1970 | Burgoa | F17C 13/126 |
| | | | | 220/592.25 |

(Continued)

FOREIGN PATENT DOCUMENTS

CN 205746022 U 11/2016

OTHER PUBLICATIONS

SANTOCEL (Year: 2020).*

(Continued)

*Primary Examiner* — Paul Alvare
(74) *Attorney, Agent, or Firm* — Brown & Michaels, PC

(57) ABSTRACT

A closure is configured for use with a portable cryogenic container or dewar, such as a dry vapor shipper (DVS). The closure has advanced insulating properties which enhances cryogen residence time and also minimizes negative effects on residence time when the dewar is placed on its side, such as during shipping. The closure includes a gas vent in the form of a fluid passage which is particularly sized to minimize thermal leakage and located away from the closure-to-neck interface. Embedded electronics can detect, record, and/or communicate information pertinent to a condition of the storage container in which the closure is installed.

17 Claims, 2 Drawing Sheets

(56) References Cited

U.S. PATENT DOCUMENTS

| | | | | |
|---|---|---|---|---|
| 3,538,714 | A | * | 11/1970 | Klipping ............... F17C 13/005 220/592.27 |
| 3,628,347 | A | * | 12/1971 | Puckett .................... F25D 3/10 62/48.1 |
| 3,750,414 | A | | 8/1973 | Heftman |
| 3,938,346 | A | * | 2/1976 | Ovchinnikov ............ F17C 3/08 62/47.1 |
| 4,790,141 | A | * | 12/1988 | Glascock .................. F17C 3/02 62/51.1 |
| 5,856,172 | A | * | 1/1999 | Greenwood ............. C12N 1/04 435/243 |
| 6,036,045 | A | | 3/2000 | West |
| 6,119,465 | A | * | 9/2000 | Mullens ................... A01N 1/02 62/371 |
| 9,518,898 | B2 | | 12/2016 | Jimenez-Rios |
| 2001/0052531 | A1 | | 12/2001 | Randall et al. |
| 2002/0114937 | A1 | * | 8/2002 | Albert ................ C04B 38/0022 428/304.4 |
| 2005/0016198 | A1 | | 1/2005 | Wowk et al. |
| 2006/0260328 | A1 | | 11/2006 | Rampersad |
| 2010/0299278 | A1 | * | 11/2010 | Kriss .................. G06Q 10/0833 705/332 |
| 2011/0143452 | A1 | | 6/2011 | Che et al. |
| 2012/0318808 | A1 | * | 12/2012 | McCormick .......... F16L 59/065 220/592.21 |
| 2012/0325826 | A1 | * | 12/2012 | McCormick ............ A61M 5/44 220/592.01 |
| 2014/0150422 | A1 | | 6/2014 | Brown et al. |
| 2014/0263358 | A1 | | 9/2014 | Espinosa-Loza et al. |
| 2017/0030626 | A1 | * | 2/2017 | Closs ................... A01N 1/0252 |

OTHER PUBLICATIONS

International Search Report on International Application No. PCT/US18/49076, dated Nov. 15, 2018, 5 pages.

Written Opinion on International Application No. PCT/US18/49076, dated Nov. 15, 2018, 10 pages.

* cited by examiner

CRYOGENIC STORAGE CONTAINER CLOSURE

TECHNICAL FIELD

The present disclosure relates generally to insulated storage containers and, in particular, to cryogenic storage containers and components.

BACKGROUND

Cryogenic storage dewars are thermally insulated containers designed to temporarily store a cryogenic liquid and, in some cases, frozen contents that must be kept at or near cryogenic temperatures during storage. For example, certain life science products may be kept at cryogenic temperatures to maintain post-thaw viability. When the products are needed for use, such as in cell therapy treatment, a portable dewar may accommodate transport and delivery of the products to the bedside of a patient while continuing to maintain the desired cryogenic temperature. Due to the extremely low boiling point of cryogenic liquids and the unavoidable imperfection in thermal insulation of the dewar, any given amount of cryogenic liquid has a finite time beyond which it is completely vaporized when the dewar is in an environment above its boiling point. Furthermore, due to the very large temperature differential between the boiling point of the cryogen and typical ambient temperatures, the volumetric expansion of cryogenic liquids during that time is extremely high, quickly leading to high internal pressure if the liquid boils off in a closed space.

Some dewars are specially designed as high-pressure metal storage vessels that use the evaporated cryogen to equalize the vapor pressure of the remaining liquid to keep it in the liquid state. Such containers are heavy and expensive, requiring safety relief valves to prevent catastrophic failure of the pressure vessel. Other types of dewars simply have an open top that allows the vaporized cryogen to freely escape to the atmosphere. While open-top dewars are less expensive and can be made more portable, the residence time of the cryogen as a liquid is very short, and they are not suitable for shipping. Some dewars can be equipped with a loose-fitting stopper or cork with large amounts of clearance between the dewar neck and the stopper so that evaporated cryogen can exit the dewar without excessive pressure build-up. While a theoretical improvement over an open-top dewar with respect to cryogen residence time, such stoppers in practice act merely as caps that prevent outside materials from falling into the dewar because the clearance between the stopper and the dewar neck is so large that it negates any insulative properties of the stopper. These types of stoppers are also unsuitable for shipping because the cryogen liquid or heavier-than-air cryogen vapor will spill out between the loose-fitting cap and dewar neck if the container is tipped over onto its side.

SUMMARY

In accordance with one embodiment, a closure for a cryogenic storage container has an outer perimeter. The cryogenic storage container has a storage cavity and a neck extending from the storage cavity to an open end. The outer perimeter of the closure forms a fluid-tight seal with the neck of the container when the closure is in an installed position in the neck of the storage container.

In some embodiments, the closure includes a hollow body and one or more super-insulating panels located within the hollow body and between the storage cavity and an exterior of the storage container when the closure is in the installed position. The one or more super-insulating panels may include an aerogel material, and the one or more super-insulating panels may include a plurality of overlapping panels made from an aerogel material.

In some embodiments, the closure includes a fluid passage fluidly connecting the storage cavity with an environment outside of the storage container when the closure is installed in the neck of the container. The fluid passage has an end located at the storage cavity and away from and within the outer perimeter of the closure. A ratio of a maximum cross-sectional area of the fluid passage to a minimum cross-sectional area of the neck may be less than 0.20 and may be 0.01 or less in some embodiments. The closure may include a heat sink at an opposite end of the fluid passage. The heat sink is configured to prevent blockage of the fluid passage at said opposite end due to ice formation.

In some embodiments, the closure includes an electronic device and an electrical power source configured to power the electronic device. The electronic device is configured to provide information pertinent to a condition of the storage container in which the closure is installed. The electronic device may include a wireless transmitter configured to transmit the information to an external receiver, a datalogger configured to record the information, or a global positioning system component.

In some embodiments, the closure includes a temperature sensor configured to measure a temperature of the storage cavity when the closure is in the installed position.

In some embodiments, the closure includes a sensor configured to produce a signal when the closure is moved away from the installed position.

In some embodiments, the closure includes a sensor configured to produce a signal when an orientation of the closure is changed.

In some embodiments, the closure includes a thermoplastic body configured to be inserted through the open end and into the neck of the storage container when moved from an uninstalled position to the installed position. The thermoplastic body partly defines the storage cavity and faces an inner perimeter of the neck when the closure is in the installed position.

In some embodiments, the thermoplastic body comprises a polyester copolymer.

In some embodiments, the thermoplastic body comprises a layer of thermoplastic foam between layers of thermoplastic film.

In some embodiments, the closure includes a sealing element defining the outer perimeter. The sealing element forms the fluid-tight seal with the neck of the container when the closure is in the installed position.

In accordance with another embodiment, a closure for a cryogenic storage container includes a head, a body, a sealing surface, an aerogel material, and a vent. The cryogenic storage container has a storage cavity and a neck extending from the storage cavity to an open end. The head and the body are joined at a shoulder. The body extends from the shoulder to a free end and has a hollow portion between the shoulder and the free end. The head extends from the shoulder in a direction away from the free end of the body. The sealing surface is located along and circumscribes the body and is configured to form a fluid-tight seal with the neck of the container when the closure is in an installed position with the shoulder at the open end of the neck. The aerogel material is enclosed in the hollow portion of the body. The vent has a first open end at the free end of the body and extends through the body from the first open end to a second open end. The first and second open ends are on opposite sides of the hollow portion of the body. The aerogel material has an opening formed therethrough, and the vent passes through the opening so that, when the closure is in the installed position, the storage cavity is fluidly connected to an environment outside of the storage container.

In some embodiments, the closure includes a shell removably attached to the body. The shell partly defines a cavity between the shell and the body. The closure includes at least one electronic device located in the cavity between the shell and the body. The at least one electronic device is configured to provide information pertinent to a condition of the storage container in which the closure is removably installed. Said condition includes at least one of: a global position, a container identifier, a storage cavity temperature, an orientation, an elapsed time, an open or closed state, or a history of any of the preceding conditions.

In accordance with another embodiment, a cryogenic storage container includes the closure. The cryogenic storage container includes a storage cavity and a neck extending from the storage cavity to an open end. The cryogenic storage container is a dry vapor shipper including a porous material adjacent the storage cavity. The porous material is configured to contain liquid cryogen and release evaporated cryogen into the storage cavity.

Various aspects, embodiments, examples, features and alternatives set forth in the preceding paragraphs, in the claims, and/or in the following description and drawings may be taken independently or in any combination thereof. For example, features disclosed in connection with one embodiment are applicable to all embodiments in the absence of incompatibility of features

BRIEF DESCRIPTION OF THE DRAWINGS

One or more embodiments will hereinafter be described in conjunction with the appended drawings, wherein like designations denote like elements, and wherein.

DESCRIPTION OF ILLUSTRATIVE EMBODIMENTS

Described below is a closure configured for use with a portable cryogenic container or dewar, such as a dry vapor shipper (DVS). The closure has advanced insulating properties which enhances cryogen residence time and also minimizes negative effects on residence time when the dewar is placed on its side, such as during shipping. The closure includes a gas vent in the form of a fluid passage which is particularly sized to minimize thermal leakage and located away from the closure-to-neck interface. Embedded electronics can detect, record, and/or communicate information pertinent to a condition of the storage container in which the closure is installed.

Figure 1:
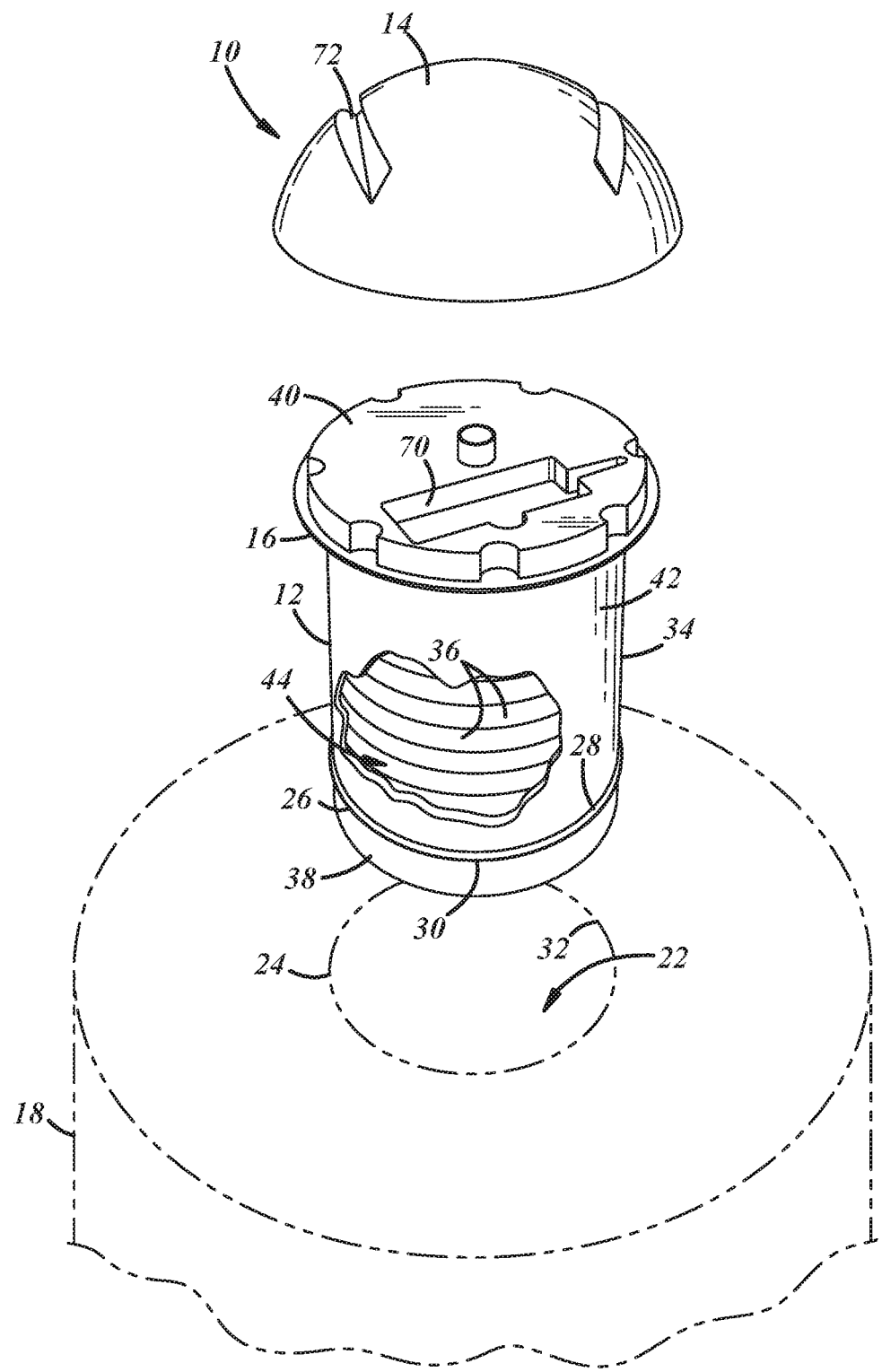
FIG. 1 is a partially exploded view of an embodiment of a closure for use with a cryogenic storage container, with a body of the closure shown in a cutaway view.

FIG. 1 is a partially exploded view of an embodiment of a closure 10 including a hollow body 12, shown in a partial cutaway view, and a head 14 that is joined to the body 12 at a shoulder 16. The closure 10 is sized, shaped, and configured for use with a cryogenic container or dewar 18, a portion of which is illustrated in phantom view in FIG. 1 and in cross-section in FIG. 2. The container 18 includes a closable storage cavity 20 and a neck 22 extending from the storage cavity to an open end 24. The dewar 18 is configured to contain a cryogenic liquid within the storage cavity 20 and/or within porous walls adjacent and at least partially surrounding the storage cavity.

As used herein, a cryogenic liquid is a liquified gas that has a boiling point less than or equal to −150° C. The cryogenic fluid may be referred to as a cryogen in either liquid or gaseous states. Liquid nitrogen (LN2) has a boiling point of −196° C. and is one example of a cryogenic liquid. Other examples of gases that can be liquified to cryogenic liquids include helium, hydrogen, neon, nitrogen, oxygen, and air.

Figure 2:
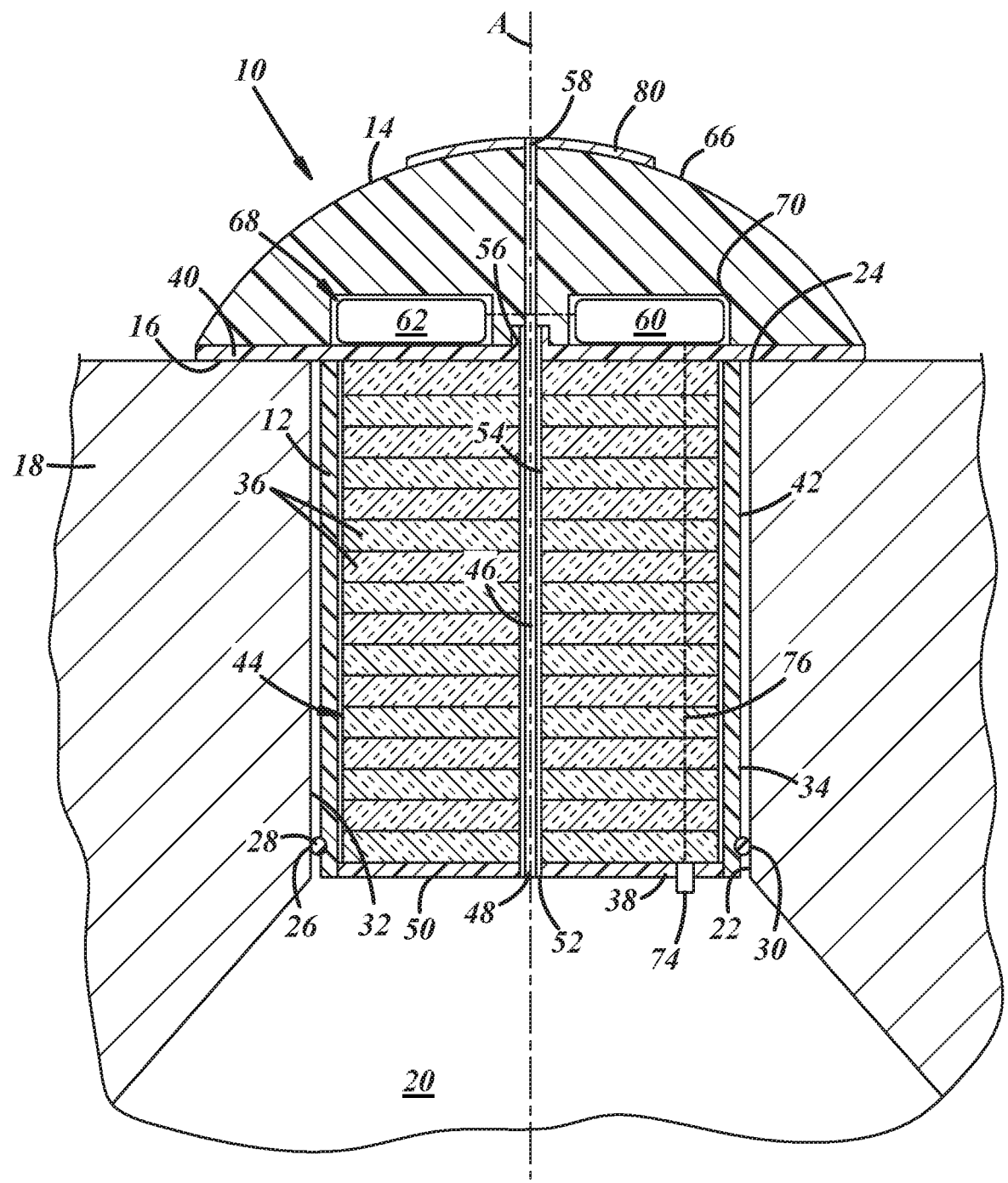
FIG. 2 is a cross-sectional view of an embodiment of the closure.

The closure 10 has an installed position and an uninstalled position with respect to the container 18. In the installed position, an outer perimeter 26 of the closure 10 forms a fluid-tight seal with the neck 22 of the container 18, unlike conventional loose-fitting dewar stoppers described above. In the uninstalled position, the fluid-tight seal is broken, such as when the closure 10 is not in physical contact with the container 18. FIG. 2 illustrates the closure 10 in the installed position.

In the illustrated embodiment, the outer perimeter 26 is defined by a sealing element 28, such as an elastomeric O-ring, having an outwardly facing sealing surface 30 that completely circumscribes the body 12 of the closure 10 such that the fluid-tight seal is continuous about the entire outer perimeter 26 of the body and about an entire inner perimeter 32 of the neck 22 of the container 18. The respective cross-sectional shapes of the body 12, particularly the sealing surface 30, and the neck 22 are complimentary and are circular in this example. In other examples, the separately formed sealing element 28 may be omitted and the sealing surface 30 may be provided by an outer surface 34 of the body 12 of the closure 10. In one embodiment, the difference between an outer diameter of the body 12 and an inner diameter of the neck 22 is in a range from 0.0 mm to 0.4 mm. For instance, an outer diameter of the outer surface 34 of the body may be up to 0.4 mm smaller than the inner diameter of the neck 22, with the sealing element 28 sized to fill the resulting gap between opposing surfaces of the body 12 and neck. Or an outer diameter of the sealing element 28 may be up to 0.4 mm larger than an inner diameter of the neck for a press-fit condition such that the sealing element 28 compresses when in the installed position.

The illustrated closure 10 also includes one or more super-insulating panels 36 located within the hollow body 12, between the storage cavity 20 of the container 18 and an exterior of the storage container when the closure is in the installed position. In this example, a plurality of super-insulating panels 36 are stacked together in an overlapping arrangement within the hollow body 12. As used herein, an element such as a panel or a piece of material is considered to be super-insulating if the thermal conductivity of the element is less than 0.02 W/m–K. In one embodiment, each super-insulating panel 36 is formed from an aerogel material. Suitable aerogel materials are available from Aspen Aerogels, Inc. (Northborough, Massachusetts, USA). In a non-limiting example, the number of aerogel panels stacked together within the hollow body 12 of the closure 10 is in a range from 10 to 20, with each panel being 5 mm or 10 mm in thickness. Other types of super-insulating panels 36 include vacuum panels and panels made from certain commercially available microporous materials. In some cases, a material that is super-insulating at atmospheric pressure (e.g., aerogel) is encased in a partially evacuated enclosure to form a super-insulating panel 36 with an effective thermal conductivity that is even lower than that of the encased super-insulating material. In some cases, non-vacuum super-insulating panels 36 formed from aerogel or some other material that is super-insulating at atmospheric pressure are preferred, because vacuum panels can lose some of their insulating properties if the vacuum is lost, which can happen without indication.

The illustrated body 12 includes a bottom or first wall 38, a top or second wall 40, and one or more side walls 42 extending therebetween. A hollow portion 44 of the body 12 is defined between the first and second walls 38, 40 and within a perimeter formed by the one or more side walls 42, which is a single cylindrical side wall in this example. The body 12, including any or all of the walls 38-42, may be formed from a thermoplastic material. While most thermoplastic materials have a glass transition temperature ($T_g$) above the boiling point of cryogenic liquids, which causes such materials to become brittle in the presence of a cryogen, certain thermoplastic materials and combinations of thermoplastic materials have been successfully employed as the closure body 12. In one embodiment, the body 12 is formed from a copolyester material. In another example, the body 12 is formed from a copolymer of poly(ethylene terephthalate), or co-PET. In a particular example, the body 12 is formed from a glycol-modified PET (PETG). In yet another example, at least a portion of the body is formed from a thermoplastic foam, such as a polyester copolymer foam, a co-PET foam, or a PETG foam.

In some embodiments, one or more of the walls 38-42 are formed from a multi-layer thermoplastic material having a foam material layer disposed between layers of thermoplastic film (i.e., non-foam). The foam material layer may make-up a majority of the thickness of each wall, such as from 50% to 95% of the wall thickness. For example, the wall thickness may be in a range from 0.75 mm to 1.25 mm, and each wall may be constructed from two thermoplastic film layers each having a thickness of 0.05 mm with a foam material layer making up the remainder of the thickness. Some non-limiting foam thermoplastic material thicknesses include 0.65 mm, 0.90 mm, and 1.15 mm. One or more layers of such a multi-layer wall construction can be formed from one of the above-mentioned thermoplastic materials, such as polyester-based copolymers, or from other suitable materials, which may include thermoplastic olefins (TPOs) and/or thermoplastic elastomers (TPEs), for example. Copolyester materials are commercially available under the tradenames ECOZEN™, SKYGREEN™, and SKYPET™ (SK Chemicals, Gyeonggi-do, Korea), in the XCELT™ family of materials (Artenius Italia, Udine, Italy), and under the tradenames Tritan™, Pacur™, Drystar™, Eastalite™, Eastar™, and Spectar™ (Eastman Chemical Company, Kingsport, Tennessee, USA).

In one embodiment, each of the walls 38-42 of the body 12 is thermoformed from a sheet of thermoplastic material. The illustrated side wall 42 may be formed from two or more separately thermoformed sheets in quarters, thirds, or half arc-sections, for example, then assembled to the generally parallel first and second walls 38, 40. In the illustrated example, the top wall 40 is formed with a diameter larger than the portion of the body 12 that fits inside the neck 22 of the container and thus provides the shoulder 16, which may serve as a positive stop when the closure 10 reaches the installed position. Alternatively, the shoulder 16 may be defined by the head 14 of the closure.

The illustrated closure 10 further includes a fluid passage 46 that functions as a gas vent that allows evaporated cryogen to escape from the storage cavity 20 when the closure is in the installed position and the closed container 18 contains cryogenic liquid. The fluid passage 46 has a first end 48 opening on a free end 50 of the body 12 via an aperture 52 formed through the bottom wall 38. The fluid passage 46 extends from the aperture 52 and through apertures 54 formed through each one of the super-insulating panels 36 to an aperture 56 formed through the top wall 40 of the body 12. In the example of FIG. 2, a second opposite end 58 of the fluid passage 46 is located along an exterior surface of the head 14 of the closure 10. A first or body portion of the fluid passage 46 is thus located in the body 12, and a second or head portion is located in the head 14.

In this particular example, the body portion of the fluid passage 46 is defined by a tube extending from the bottom wall aperture 52 to the top wall aperture 56, with the super-insulating panel apertures 54 being sized to have a tight fit with the tube. The head portion of the fluid passage 46 is formed directly through the head 14 and is connected with the body portion of the fluid passage at the aperture 56 in the top wall 40. In other embodiments, the head portion of the fluid passage may be omitted, and evaporated cryogen may be allowed to escape via clearance between the body 12 and head 14 of the closure 10. In some embodiments, the fluid passage 46 may include a plurality of branches formed in or through the head 14 of the closure with a corresponding plurality of openings to the exterior of the closure. Also, the separately provided tube may be omitted in some cases with the concentric and stacked apertures 54 forming an effective fluid passage on their own.

Notably, the fluid passage 46 is not formed along the interface between the body 12 of the closure and the neck 22 of the container 18. Rather, the illustrated fluid passage 46 is located entirely within the perimeter of the body 12 and, in particular, within the perimeter 26 at which the fluid-tight seal is formed between the closure 10 and the neck 22 of the container 18. In this example, the fluid passage 46 is located along a central axis A of the closure, coaxial with the body 12 and/or head 14. The fluid passage 46 allows the closure 10 to provide adequate venting of evaporated cryogen while providing several other advantages.

For example, a conventional DVS fitted with a loose-fitting stopper designed with a gap between the neck of the container and the stopper may provide a residence time of about 10 days when the dewar is fully charged with about 10 kilograms of LN2 and the dewar is kept in the upright position as a measure of the static performance of the dewar.

The same dewar and stopper configuration provides a residence time of only about 1 day for the same amount of LN2 when the dewar is oriented on its side, which is a measure of the dynamic performance of the dewar. The dynamic performance of the conventional stoppered-dewar is thus reduced by about 90% compared to the static performance. The dynamic performance of a dewar fitted with the illustrated closure 10 may be reduced by less than 10% when compared to its static performance due in part to its small size and central location. Experimental results indicate that the dynamic performance of the closure disclosed herein is equivalent to the static performance of a conventional loose-fitting stopper.

Also, conventional dewar stoppers or caps do not include the super-insulating panel(s) 36 of the illustrated closure 10, which affects sizing of the gap or gaps that surround a loose-fitting cap for venting. In other words, a poorly insulated stopper allows much more thermal energy to be transferred from the exterior of the dewar to the storage cavity. There is a direct relationship between the volume of evaporated cryogen that the closure 10 must be capable of venting to the atmosphere and the insulating capability of the closure. A stopper with a lower amount of thermal insulation (e.g., a lower R-value) leads to a greater heat transfer rate from the external environment into the storage cavity of the dewar. As the heat transfer rate increases, the evaporation rate of the cryogen increases. As the evaporation rate increases, the rate of volumetric expansion of the cryogen when changing phase from liquid to gas and warming as a gas also increases. Volumetric expansion is significant with cryogens, ranging anywhere from a 700-times increase in volume for LN2 to over a 1400-times increase in volume for neon when increasing in temperature from boiling point to ambient. As a result, the lower the insulating performance of the closure, the larger the gas vent must be to allow the gas to escape. But increasing the size of the gas vent reduces the insulating performance of the closure even further, which increases the cryogen evaporation rate even further, which requires an even larger vent, etc.

Conventional dewar caps are thus made with such large gaps between the cap and the neck of the dewar that any insulating performance associated with the cap is virtually negated. By way of example, a typical loose-fitting stopper for a dewar having a neck with an inside diameter of 178 mm (7 in.) has an outside diameter of about 152 mm (6 in.), creating a thermal leak path—i.e., a path connecting the storage cavity 20 to the external environment along which there is zero thermal insulation—that occupies over 20% of the area of the neck opening. The illustrated closure 10 allows for a ratio of the cross-sectional area of the vent (i.e., fluid passage 46) to the cross-sectional area of the neck 22 to be significantly less than 0.20, such as less than 0.10, less than 0.05, less than 0.01, and down to nearly 0.001. Indeed, an embodiment of the closure 10 has now been produced with a fluid passage 46 having a diameter of only 6 mm, the closure being configured for use in a 178 mm neck—i.e., the thermal leak path created by the gas vent occupies merely 0.1% of the area of the neck opening. Smaller vent area to neck area ratios are believed possible.

The result is more than just an increased cryogenic liquid residence time. The conservation of liquid cryogen and the improved dynamic performance achieved via use of the disclosed closure 10 is so dramatic that a dewar need only be charged with a fraction of the amount of cryogenic liquid to achieve the same or better static and dynamic performance achieved with conventional dewar stoppers. This enables use of a much smaller dewar which weighs less, costs less to transport, simplifies and speeds the cryogen charging process, and is sufficiently lightweight for easy handling by shipper, receiver, and user, while also extending the permissible shipping time.

The closure 10 may also include one or more powered electronic devices 60 and a power source 62, such as a rechargeable battery, connectable to the electronic device(s) as shown in FIG. 2. Each electronic device 60 may be configured to provide information to a user, the information being pertinent to a condition of the storage container 18 in which the closure 10 is installed. The information may be provided to the user directly or indirectly. An example of indirectly provided information is an audible alarm that indicates some condition of the container 18, such as a temperature inside the container that is too high. An example of indirectly provided information is information recorded over time and later transmitted to the user via a wireless transmission to a computer or computer network. Where more than one type of electronic device 60 is included, they may be individually provided and/or electrically connected together or they may be combined into a unitary electronics package.

Non-limiting examples of electronic devices include electronic sensors, data-loggers, a GPS unit, wireless transmitters or transceivers, and computer processors, to name a few. Non-limiting examples of sensors include temperature sensors, light sensors, accelerometers, and proximity sensors. Sensors can be electronic or non-electronic. For example, a light sensor may be photovoltaic, producing a voltage in the presence of light, or a light sensitive film that changes color when exposed to light. Non-limiting examples of information pertinent to a condition of the container include a real-time temperature or temperature-time profile of the storage cavity of the container, an orientation of the container (e.g., upright, lying on a side, upside-down, etc.), a global position of the container, an amount of elapsed time since the container was last opened, and a container identifier (e.g., a serial number or shipper identification number).

As indicated in the figures, the electronic device(s) 60 and/or the power source 62 may be housed internally within the closure 10 where the body 12 and head 14 are joined. In the illustrated examples, the head 14 of the closure is at least partly formed by a shell 66, and a cavity 68 is formed between the shell and the top wall 40 of the body 12. As shown in the example of FIG. 1, a recess 70 may be thermoformed in the body 12 to form at least part of the cavity 68 and to accommodate the size and shape of the desired electronic device(s) or power source. Additionally or alternatively, as shown in the example of FIG. 2, one or more recesses 70 may be formed in the shell 66 to form at least part of the cavity 68 and to accommodate the size and shape of the device(s) 60 or power source 62. The shell 66 is removably attached to the body 12, such as by a snap or interference fit. The electronic device(s) 60 and power source 62 may thus be isolated from the extreme temperatures of the cryogen by the super-insulating panel(s) 36 and accessible by a user without removing the closure from the installed position in the container.

The illustrated shell 66 is a monolithic component formed from a single, homogeneous and continuous piece of material with recesses 70 formed on the cavity side of the shell and handling features 72 (FIG. 1) formed on an opposite exterior side. The illustrated handling features are in the form of recesses that allow a user to grip the head 14 of the closure 10 to install or remove the closure in or from the container 18, or to separate the shell 66 from the body 12 to access the electronics and power source. In some embodiments, the shell 66 is formed from a molded polymeric foam material, such as ethylene-vinyl acetate (EVA) foam or other suitable ethylene copolymer foam, such as a TPO foam. In other embodiments, the top wall 40 of the body is removable with the shell 66.

The head 14 of the closure 10 may also include a heat sink 80 coupled with the shell 66 as shown in FIG. 2. The heat sink 80 is a layer of highly thermal conductive material such as copper, aluminum, or other suitable metal. The heat sink 80 is located adjacent the second end 58 of the fluid passage 46 and extends radially away from the fluid passage along the exterior of the shell 66 in this example. An aperture formed through the heat sink 80 thus represents the second end 58 of the fluid passage 46 in this example. In one embodiment, the heat sink is formed from 24-gauge (about 0.5 mm) aluminum or aluminum alloy and has an outer diameter of about 125 mm. The exposed surface area-to-thickness ratio is relatively large, for example greater than about 25,000 $mm^2$/mm. The heat sink 80 reduces of water vapor from the surrounding atmosphere condensing, freezing, and possibly blocking the fluid passage 46 by providing sufficient thermal mass and conductivity to heat or maintain the gas at the second end of the vent above the dew point.

The example of FIG. 2 includes a sensor 74 operably connected with the electronic device 60, which includes a data-logger capable of storing information generated by the sensor over time. The sensor 74 may include a temperature sensor and/or a light sensor, for example. A temperature sensor can be used to monitor the temperature of the storage cavity 20 of the container 18 over time for real-time or intermittent transmission to a cloud-based database, for example, or for recordation and later retrieval of a temperature-time profile of the storage cavity during shipment or storage. A light sensor can be used to monitor an open or closed condition of the container 18 over time for real-time or intermittent transmission to a cloud-based database, for example, or for recordation and later retrieval.

The illustrated sensor 74 is located at the free end 50 of the body 12 of the closure 10 for exposure to the storage cavity 20 of the container when the closure is in the installed position. An electrical connection 76 extends through the hollow portion 44 of the body 12 of the closure 10 between the electronic device 60 and the sensor 74. In this particular example, the connection 76 is a wire that extends through aligned apertures formed through each of the super-insulating panels 36, with each aperture being approximately the same size as the wire to minimize creation of a thermal leak path. In embodiments including a light sensor, the sensor may be located closer to the shoulder 16 of the closure in order to detect when the closure has been partially removed.

In some embodiments, the one or more electronic device 60 includes a GPS unit—in particular, a GPS receiver capable of determining the location of multiple GPS satellites and thereby determining the global position of the container 18 in which the closure 10 is installed. The closure 10 can thus be part of a geo-fencing system that provides alerts when the dewar has crossed pre-determined geographical thresholds to assist a recipient in accurately anticipating the arrival time of the dewar during shipping or transport. Global position can also be monitored and recorded over time during shipping and correlated with other information pertinent to container conditions during shipping. For example, global position information can be recorded when an installed light sensor indicates that the closure 10 has been tampered with or when an installed accelerometer indicates that the container 18 has been dropped or fallen over and away from the upright position.

When the electronic device 60 includes a wireless transmitter or transceiver, it may be configured for wireless communication via known protocols associated with wi-fi, mobile phone networks, LANs, WANs, and short-range wireless protocols (e.g., Bluetooth™), for example.

The disclosed closure 10 thus provides enhanced static and dynamic dewar performance and enables reductions in dewar size, weight, cost, and cryogen capacity, while additionally acting as a "smart" closure, able to provide a convenient method for real-time monitoring of the temperature within the dewar as well as the location of the dewar, for example. Real-time data and tracking information can be communicated to a cloud-based application and provide a user with valuable information such as payload temperature, dewar orientation (which can affect the cryogen residence time), chain of custody information (e.g., when or if the dewar has been opened prior to delivery, and/or geofencing alerts to notify a user or monitoring system when the dewar has crossed geographical thresholds.

Increased dynamic performance of the above-described closure compared to a conventional dewar cap has been experimentally verified with a large-mouth dry vapor shipper (DVS) having a 203 mm (8 inch) neck diameter. The conventional loose-fitting cap allowed 221 grams of LN2 per hour (53 cc/sec) to escape the DVS. A 10-kg initial charge of LN2 would thus have a residence time of less than two days—i.e., about 45 hours. A closure configured consistent with the above disclosure allowed only 42 grams of LN2 per hour (10 cc/sec) to escape the same DVS. A 10-kg initial charge of LN2 would thus have a residence time of about 10 days—i.e., about 238 hours. Static performance increases are expected to be even higher.

It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A closure for a cryogenic storage container having a storage cavity and a neck extending from the storage cavity to an open end, the closure comprising:
   a body;
   a shoulder;
   a head removably joined with the body at the shoulder, the body extending from the shoulder to a free end and having a hollow portion between the shoulder and the free end, the head extending from the shoulder in a direction away from the free end of the body;
   a cavity defined between the head and the body;
   at least one electronic device located in the cavity between the head and the body, the at least one electronic device being configured to provide information pertinent to a condition of the storage container in which the closure is removably installed, wherein said condition includes at least one of: a global position, a container identifier, a storage cavity temperature, an orientation, an elapsed time, an open or closed state, or a history of any of the preceding conditions;
   a sealing surface located along and circumscribing the body, the sealing surface being configured to form a fluid-tight seal with the neck of the container when the closure is in an installed position with the shoulder at the open end of the neck, the fluid-tight seal being continuous about an entirety of the sealing surface to form a closed circumscription about the entirety of the sealing surface;

an aerogel material enclosed in the hollow portion of the body; and a vent having a first open end at the free end of the body and extending through the body from the first open end to a second open end, the first and second open ends being on opposite sides of the hollow portion of the body, wherein the aerogel material has an opening formed therethrough and the vent passes through the opening so that, when the closure is in the installed position, the storage cavity is fluidly connected to an environment outside of the storage container.

2. A cryogenic storage container comprising the closure of claim 1, the cryogenic storage container further comprising a storage cavity and a neck extending from the storage cavity to an open end, wherein the cryogenic storage container is a dry vapor shipper comprising a porous material adjacent the storage cavity, the porous material being configured to contain liquid cryogen and release evaporated cryogen into the storage cavity.

3. The closure of claim 1, further comprising a heat sink at the first open end of the vent, the heat sink being configured to prevent blockage of the vent at the first open end due to ice formation.

4. The closure of claim 3, wherein the head has a first thermal conductivity and the heat sink has a second thermal conductivity and is in contact with the head, the first thermal conductivity less than the second thermal conductivity.

5. A closure for a cryogenic storage container having a storage cavity and a neck extending from the storage cavity to an open end, the closure comprising:
 a body;
 a shoulder;
 a head removably joined with the body at the shoulder, the body extending from the shoulder to a free end and having a hollow portion between the shoulder and the free end, the head extending from the shoulder in a direction away from the free end of the body;
 a cavity defined between the head and the body;
 at least one electronic device located in the cavity between the head and the body, the at least one electronic device being configured to provide information pertinent to a condition of the storage container in which the closure is removably installed, wherein said condition includes at least one of: a global position, a container identifier, a storage cavity temperature, an orientation, an elapsed time, an open or closed state, or a history of any of the preceding conditions;
 a sealing surface located along and circumscribing the body, the sealing surface being configured to form a fluid-tight seal with the neck of the container when the closure is in an installed position with the shoulder at the open end of the neck;
 an aerogel material enclosed in the hollow portion of the body; and a vent having a first open end at the free end of the body and extending through the body from the first open end to a second open end, the first and second open ends being on opposite sides of the hollow portion of the body, wherein the aerogel material has an opening formed therethrough and the vent passes through the opening so that, when the closure is in the installed position, the storage cavity is fluidly connected to an environment outside of the storage container.

6. The closure of claim 5, wherein the aerogel material includes a plurality of super-insulating panels.

7. The closure of claim 5, wherein the aerogel material includes a plurality of overlapping panels.

8. The closure of claim 5, wherein a ratio of a maximum cross-sectional area of the vent to a minimum cross-sectional area of the neck is less than 0.20.

9. The closure of claim 8, wherein the ratio is 0.01 or less.

10. The closure of claim 5, further comprising an electrical power source configured to power the at least one electronic device.

11. The closure of claim 5, wherein the at least one electronic device comprises a wireless transmitter configured to transmit said information to an external receiver, a data-logger configured to record said information, or a global positioning system component.

12. The closure of claim 5, further comprising a thermoplastic body configured to be inserted through the open end and into the neck of the storage container when moved from an uninstalled position to the installed position, wherein the thermoplastic body partly defines the storage cavity and faces an inner perimeter of the neck when the closure is in the installed position.

13. The closure of claim 12, wherein the thermoplastic body comprises a polyester copolymer.

14. The closure of claim 12, wherein the thermoplastic body comprises a layer of thermoplastic foam between layers of thermoplastic film.

15. A cryogenic storage container comprising the closure of claim 5, the cryogenic storage container further comprising a storage cavity and a neck extending from the storage cavity to an open end, wherein the cryogenic storage container is a dry vapor shipper comprising a porous material adjacent the storage cavity, the porous material being configured to contain liquid cryogen and release evaporated cryogen into the storage cavity.

16. The closure of claim 5, further comprising a heat sink at the first open end of the vent, the heat sink being configured to prevent blockage of the vent at the first open end due to ice formation.

17. The closure of claim 16, wherein the head has a first thermal conductivity and the heat sink has a second thermal conductivity and is in contact with the head, the first thermal conductivity less than the second thermal conductivity.

* * * * *